United States Patent
Funamura et al.

(10) Patent No.: US 7,618,072 B2
(45) Date of Patent: Nov. 17, 2009

(54) CONNECTING STRUCTURE OF CONNECTOR

(75) Inventors: Shigeaki Funamura, Fukuroi (JP); Ichiro Kitani, Fukuroi (JP)

(73) Assignee: Tyco Healthcare Group LP, Mansfield, MA (US)

( * ) Notice: Subject to any disclaimer, the term of this patent is extended or adjusted under 35 U.S.C. 154(b) by 46 days.

(21) Appl. No.: 11/840,641

(22) Filed: Aug. 17, 2007

(65) Prior Publication Data

US 2008/0054632 A1 Mar. 6, 2008

(30) Foreign Application Priority Data

Aug. 31, 2006 (JP) ............................. 2006-235517

(51) Int. Cl.
*F16L 25/00* (2006.01)
(52) U.S. Cl. ........................ 285/386; 285/93; 604/533; 604/535
(58) Field of Classification Search .................. 285/93, 285/332.1, 386; 604/533–534, 535
See application file for complete search history.

(56) References Cited

U.S. PATENT DOCUMENTS 4,617,012 A * 10/1986 Vaillancourt .................. 604/29
4,629,455 A * 12/1986 Kanno ......................... 604/241
5,176,415 A * 1/1993 Choksi ........................ 285/331
5,286,067 A * 2/1994 Choksi .......................... 285/38
5,782,505 A * 7/1998 Brooks et al. ........... 285/148.19
6,152,913 A * 11/2000 Feith et al. ................... 604/533
6,165,149 A * 12/2000 Utterberg et al. ........... 604/5.01
6,709,424 B1 * 3/2004 Knierbein .................... 604/411
2005/0159710 A1 * 7/2005 Utterberg .................... 604/256
2006/0157984 A1 7/2006 Rome et al.

FOREIGN PATENT DOCUMENTS

DE 4318101 A1 12/1994

OTHER PUBLICATIONS

European Search Report, Application No. 07113102.3-2310, dated Dec. 27, 2007, 6 pages.

* cited by examiner

*Primary Examiner*—Aaron M Dunwoody
*Assistant Examiner*—Fannie Kee

(57) ABSTRACT

A connection structure is provided having a female thread formed on the inner peripheral surface of a lock ring in a male connector engaging a male thread on the outer peripheral surface of a female connector when the male connector and the female connector are screwed to each other. Further, protrusion strips are formed on the rear side portion of the male thread on the outer peripheral surface of the female connector, and the notches that can engage with the protrusion strips are set on the tip portion of the lock ring. As a result, when the male thread and the female thread are screwed to each other, the screwed state is appropriate when the protrusion strips and notches are engaged with each other.

5 Claims, 4 Drawing Sheets

CONNECTING STRUCTURE OF CONNECTOR

FIELD OF THE INVENTION

The present invention pertains to a novel structure for linking a male connector and a female connector in a transfusion line.

BACKGROUND OF THE INVENTION

In the prior art, liquid medicine, blood or the like is fed into a patient by means of a solution transfusion line or a blood transfusion line equipped with tubes. In such case, the connecting structure of a connector is adopted to connect various tubes that form the transfusion line or the like (for example, see Patent Reference 1). Said medical connecting unit (connecting structure of the connector) has a male connecting unit and a female connecting unit connected to the end portions of the tubes to be connected to each other.

The male connecting unit is composed of a connecting pipe having a luer tapered outer wall and an outer cap surrounding said connecting pipe. The female connecting unit is formed as a cylindrical body that can be inserted into the outer cap, and it allows fitting of the connecting pipe to its interior. Additionally, thread strips are formed on the inner wall of the outer cap, and thread strips that can be engaged with the thread strips of said outer cap are formed on the outer wall of the female connecting unit. As a result, while the connecting pipe is fit in the female connecting unit, the outer cap can be rotated so that the thread strips engage with each other and the male connecting unit and female connecting unit can be connected to each other; see [Patent Reference 1] Japanese Kokai Patent Application No. Hei 5[1993]-31180

However, the aforementioned medical connecting unit has some problems. If the thread strips are engaged too tightly with each other, cracks develop on the female connecting unit, leading to leakage of liquid. On the other hand, if they are engaged too loosely, the connection breaks, or the connection between the male connecting unit and the female connecting unit slackens, leading to generation of a gap between them and thus leakage of the liquid flowing inside.

The object of the present invention is to solve the aforementioned problems of the prior art by providing a connecting structure of a connector that can prevent cracks and leakage of liquid.

SUMMARY OF THE INVENTION

In one aspect of the present invention, a connecting structure of a connector has, in the connecting structure of the connector, a female thread formed on the inner peripheral surface of a lock ring equipped with a male-side connector connected to one tube body and a male thread formed on the outer peripheral surface of a female-side connector connected to another tube body. The male-side and female-side connectors are screwed to each other, so that said one tube body and said other tube body are connected to each other via said male-side connector and said female-side connector. An engagement protrusion is set to the rear of said male thread on the outer peripheral surface of said female-side connector. A notch portion that can engage with said engagement protrusion is set on the tip portion of said lock ring. When said male thread and said female thread are screwed together, said engagement protrusion and said notch portion are engaged with each other.

Figure 1:
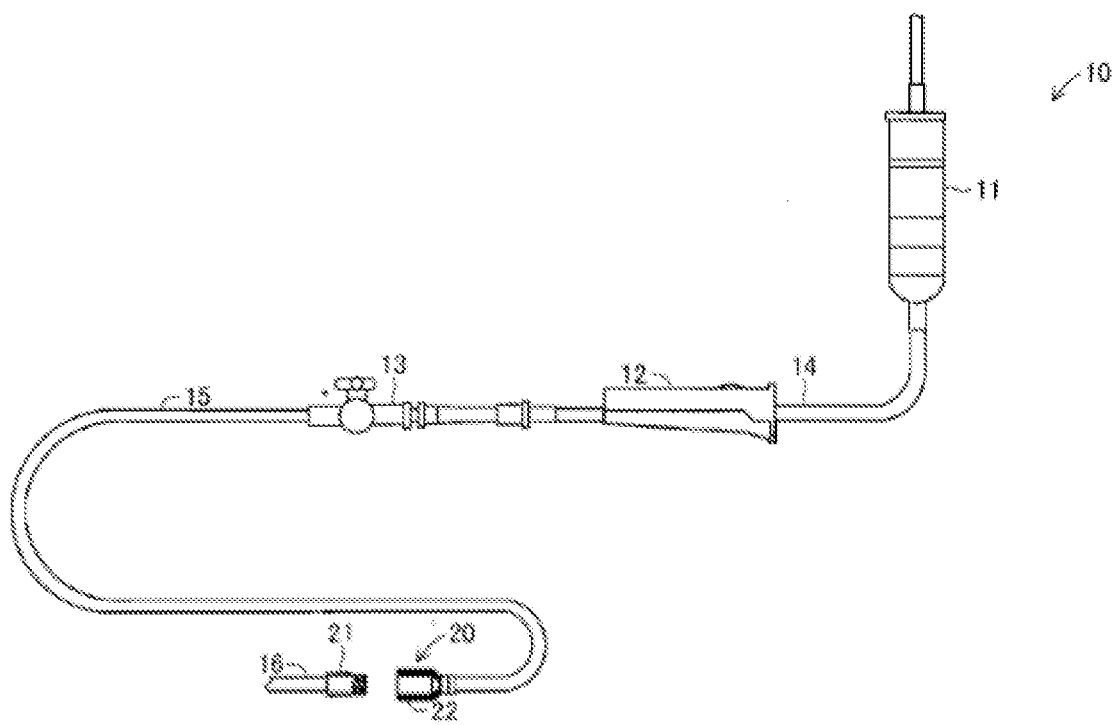
FIG. 1 is a diagram illustrating the constitution of a transfusion line set having a connection structure pertaining to an embodiment of the present invention.

EXPLANATION OF REFERENCE SYMBOLS 15, 16 Tube
20 Connection structure of connector
21 Female connector
22 Male connector
23*a* Inner peripheral surface
26*a*, 26*b* Engagement protrusion strip
27 Male connector main body
28 Lock ring
31 Supporting part
32 Male luer part
33 Connecting part
35*a*, 35*b* Notch

DETAILED DESCRIPTION OF THE INVENTION

The present invention is directed to a connecting structure of a connector. In an embodiment of the present invention, FIG. 1 is a diagram illustrating transfusion line set (10) having connecting structure (20) of a connector in said embodiment. This transfusion line set (10) is for feeding liquid medicine or the like to the body of a patient. It has infusion cylinder (11), lock clamp (12), and three-way cock (13). Said infusion cylinder (11) temporarily stores the liquid medicine or the like, and, at the same time, with each use it feeds a prescribed quantity of the liquid medicine or the like through tube (14) to the side of lock clamp (12) on the downstream side. Said lock clamp (12) is for adjustment of the flow rate of the liquid medicine or the like flowing in tube (14).

On the other hand, three-way cock (13) is for feeding or stopping the flow of the liquid medicine fed from infusion cylinder (11) to the downstream side, and, at the same time, for injecting another liquid medicine into transfusion line set (10). That is, three-way cock (13) has three flow channels. Among them, two flow channels are for feeding the liquid medicine sent from infusion cylinder (11) to the downstream side, and the remaining flow channel is used for injecting said another liquid medicine to the cock interior. On the downstream side of three-way cock (13), connecting structure (20) of connector is set via tubes (15), (16).

Figure 2:
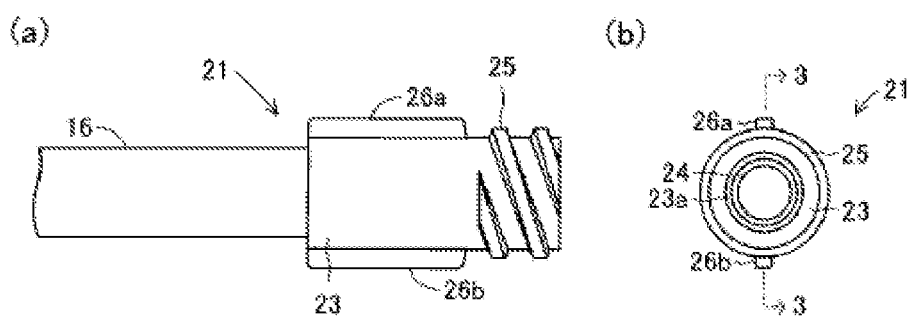
FIG. 2 illustrates the female connector, (*a*) is a side view, and (*b*) is a front view.
Figure 3:
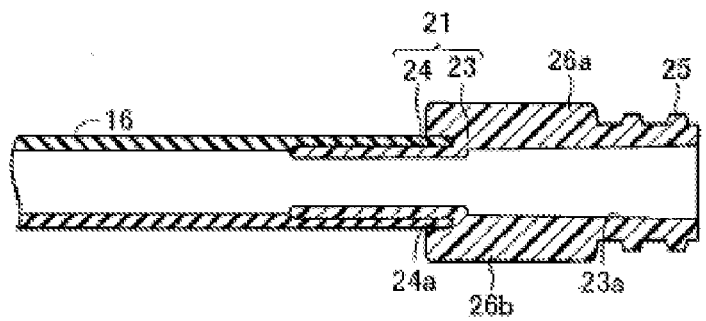
FIG. 3 is a cross-sectional view taken across line 3-3 in FIG. 2(*b*).

The connecting structure (20) of the connector is composed of female connector (21) attached on the tip portion of tube (16) and male connector (22) attached on the tip portion of tube (15). As shown in FIGS. 2 and 3, said female connector (21) is composed of thick-wall cylindrical female connector main body (23) and connecting portion (24) that extends from the rear end portion of female connector main body (23) (the base end portion positioned on the left side of FIGS. 2(a) and 3) to the rear side.

Additionally, male thread (25) is formed from the tip portion (the right side in FIGS. 2(a) and 3) to the central portion on the outer periphery of female connector main body (23). Further, on the outer peripheral surface of female connector main body (23) and in the portion from the site at a small spacing from the rear end portion of male thread (25) to the rear end portion, a pair of engagement protrusion strips (26a), (26b) are formed as engagement protrusions of the present invention in facing portions in the circumferential direction. Said engagement protrusion strips (26a), (26b) consist of protrusion strips extending in the axial direction of female connector main body (23). The outer diameter of the portion where said engagement protrusion strips (26a), (26b) are formed on female connector main body (23) is selected to be a little larger than the outer diameter of the portion where male thread (25) is formed.

An inner peripheral surface (23a) (female luer portion) of female connector main body (23) is formed as a curved surface with a larger diameter at the opening side and tapered smaller as the position moves deeper. A connecting portion (24) with a diameter smaller than that of female connector main body (23) is formed extending to the rear side from a portion slightly trailing the rear portion on inner peripheral surface (23a) of female connector main body (23). As a result, gap (24a) is formed between the inner peripheral surface of the base end portion of female connector main body (23) and the outer peripheral surface of a portion of connecting portion (24) on the side of female connector main body (23). When the tip portion of tube (16) is engaged with said gap (24a), female connector (21) is connected to tube (16). In other words, when connecting portion (24) enters the interior of tube (16), the base end portion of female connector main body (23) is held and fixed by connecting portion (24) with the tip portion of tube (16) within the interior.

Figure 4:
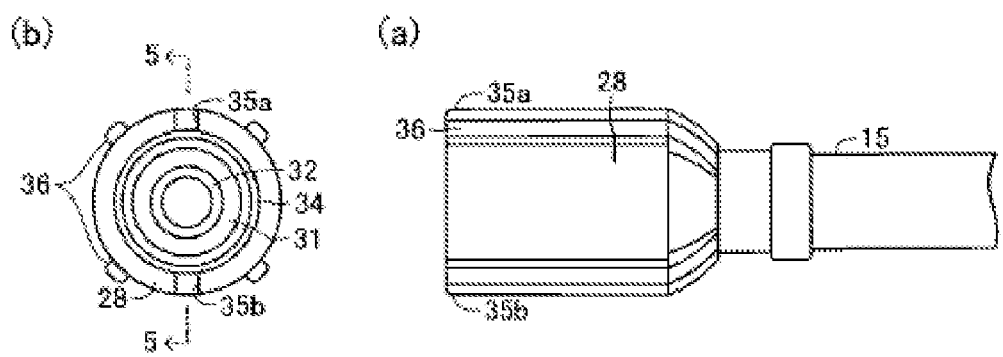
FIG. 4 illustrates the male connector, (*a*) is a side view, and (*b*) is a front view.
Figure 5:
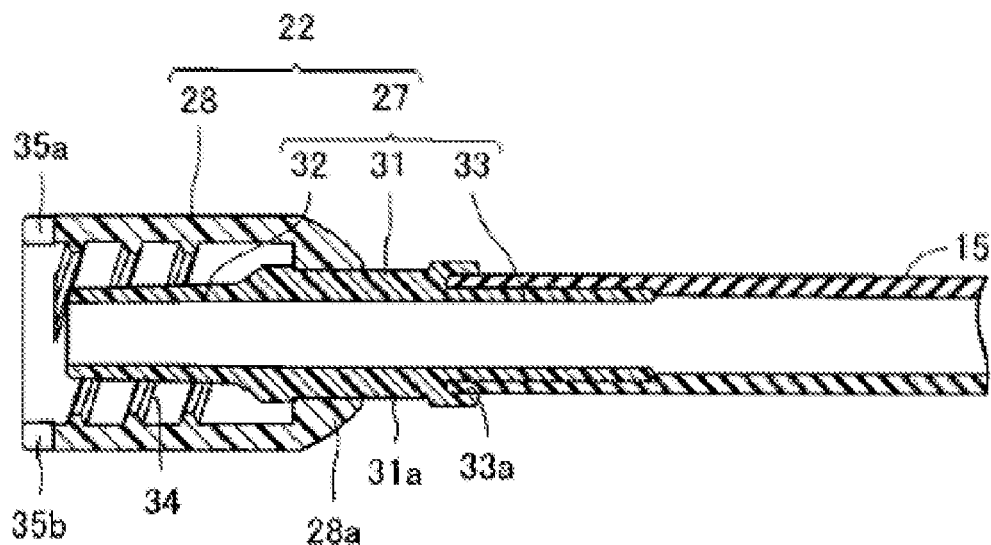
FIG. 5 is a cross-sectional view taken across line 5-5 of FIG. 4(*b*).
Figure 6:
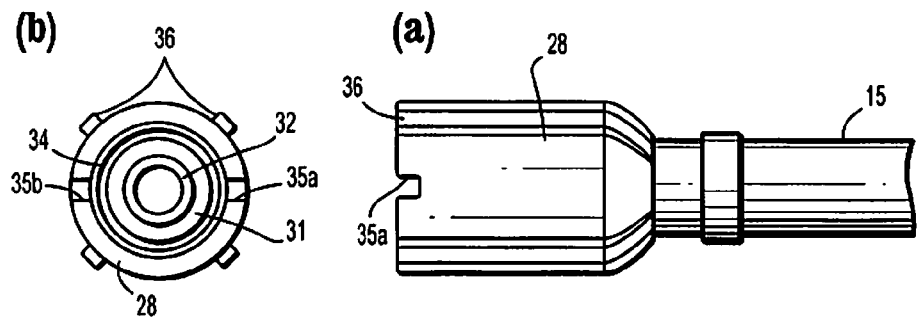
FIG. 6 illustrates a state of rotation of the lock ring equipped in the male connector shown in FIG. 4, (*a*) is a side view, and (*b*) is a front view.

As shown in FIGS. 4-6, said male connector (22) is composed of male connector main body (27) formed in a nearly cylindrical shape and lock ring (28) attached on the outer peripheral side of said male connector main body (27) and rotatable round the axis with respect to said male connector main body (27). FIG. 6 is a diagram illustrating a state in which lock ring (28) shown in FIG. 4 has been rotated by 90° around the axis with respect to male connector main body (27). Said male connector main body (27) is composed of supporting part (31) formed in a thick wall cylindrical shape, cylindrical male luer part (32) extending from the tip portion of said supporting part (31) forward and formed with a thinner wall than that of supporting part (31), and cylindrical connecting part (33) extending from the base end portion of supporting part (31) backward and formed with a thinner wall than that of supporting part (31).

Here, in order to facilitate explanation, for female connector (21), as shown in FIGS. 2(a) and 3, the left side is taken as the rear side or base end side, and the right side is taken as the front side or tip side. For said male connector (22), as shown in FIGS. 4(a), 5 and 6(a), the left side is taken as the front side or tip side, and the right side is taken as the rear side or base end side. As the outer peripheral surface of male luer part (32), a curved surface with a larger diameter on the base end side and with the diameter gradually tapered smaller towards the tip side is formed, so that it can fit liquid tight against inner peripheral surface (23a) of female connector main body (23).

Further, when male luer part (32) is fit to female connector main body (23), said female connector (21) and male connector (22) are connected to each other. Additionally, a steep tapered portion is formed on the side of male luer part (32) in supporting part (31), with the outer diameter of supporting part (31) selected larger than the outer diameter of male luer part (32). Further, on the central portion of said supporting part (31) in the axial direction, recessed portion (31a) is formed with a smaller outer diameter than that of the two end portions. Here, connecting part (33) extends from the side of the rear portion of supporting part (31) backward. For said connecting part (33), its inner diameter is selected to be identical to that of supporting part (31) and male luer part (32), and its outer diameter is selected to be nearly identical to the fine diameter portion of male luer part (32) (without a taper).

The outer diameter of connecting part (33) is selected to be smaller than the outer diameter of supporting part (31). Here, in the boundary portion between supporting part (31) and connecting part (33), ring-shaped fixing recession (33a) is formed extending from the boundary portion between the base end portion of supporting part (31) to connecting part (33) towards the tip side, and, by coupling the tip portion of tube (15) to said fixing recession (33a), male connector (22) is connected to tube (15). That is, connecting part (33) enters the interior of tube (15), and the base end portion of supporting part (31) holds and fixes tube (15) together with connecting part (33) while the tip portion of said tube enters its interior.

Said lock ring (28) is formed in a nearly cylindrical shape such that the tip portion of female connector (21) can be accommodated inside it, and the side of base end portion (28a) is formed with a smaller diameter. That is, for said lock ring (28), the size is selected such that the tip portion of female connector (21) can enter the portion between it and said male luer part (32), and its base end portion (28a) is engaged with recessed portion (31a) of supporting part (31) in a slidable way. As a result, lock ring (28) can be rotated around the axis with respect to male connector main body (27), and, at the same time, it can move in the axial direction of male connector main body (27).

Additionally, on the inner peripheral surface of lock ring (28), female thread (34) that can be screwed with male thread (25) of female connector (21) is formed from a portion at a prescribed distance from the tip portion to the central portion in the axial direction. Engagement protrusion strips (26a), (26b) of female connector (21) and, on the tip portion of lock ring (28), a pair of notches (35a), (35b) that can be engaged with said engagement protrusion strips, are formed on facing positions in the circumferential direction, respectively. The peripheral portions of said notches (35a), (35b) are formed such that the tip surface, inner surface and outer surface of lock ring (28) are opened, and they are selected such that the width in the circumferential direction is a little larger than the width of said engagement protrusion strips (26a), (26b).

Further, when male thread (25) and female thread (34) are screwed to each other, before the screwed state between male thread (25) and female thread (34) becomes appropriate (if they are screwed too tightly, liquid leakage may take place), the peripheral portions of notches (35a), (35b) climb over corresponding engagement protrusion strips (26a), (26b), respectively, and notches (35a), (35b) engage with the corresponding engagement protrusion strips (26a), (26b), respectively. Then, while notches (35a), (35b) are engaged with corresponding engagement protrusion strips (26a), (26b), the screwed state of male thread (25) and female thread (34) reaches an appropriate state. Further still, when notches (35a), (35b) are engaged with corresponding engagement protrusion strips (26a), (26b), respectively, a "CLICKING" sound can be heard. As a result, a worker can confirm the state of connection between female connector (21) and male connector (22).

Additionally, the constitution is such that when notches (35a), (35b) are engaged with corresponding engagement protrusion strips (26a), (26b), respectively, male thread (25) and female thread (34) cannot be further over-screwed. As a result, it is possible to maintain an appropriate connection state between female connector (21) and male connector (22). On the outer peripheral surface of lock ring (28), protrusion strips (36) extending in the axial direction for preventing slippage are formed at a prescribed interval in the circumferential direction. Here, female connector (21), male connector main body (27) and lock ring (28) that form connecting structure (20) of the connector are made of polycarbonate.

Figure 7:
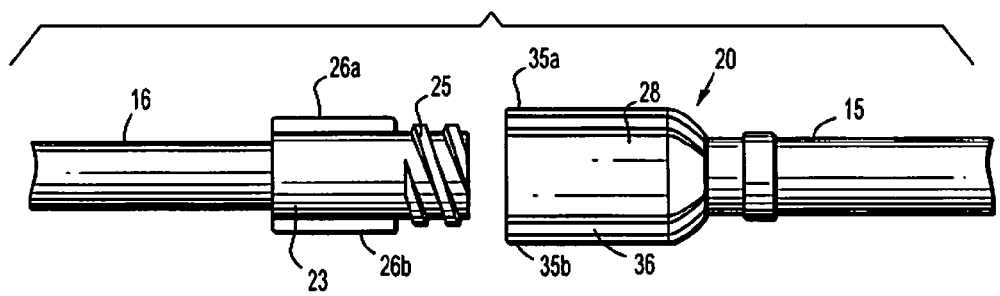
FIG. 7 is a side view illustrating the connection structure of the connector before connection between the female connector and the male connector.
Figure 8:
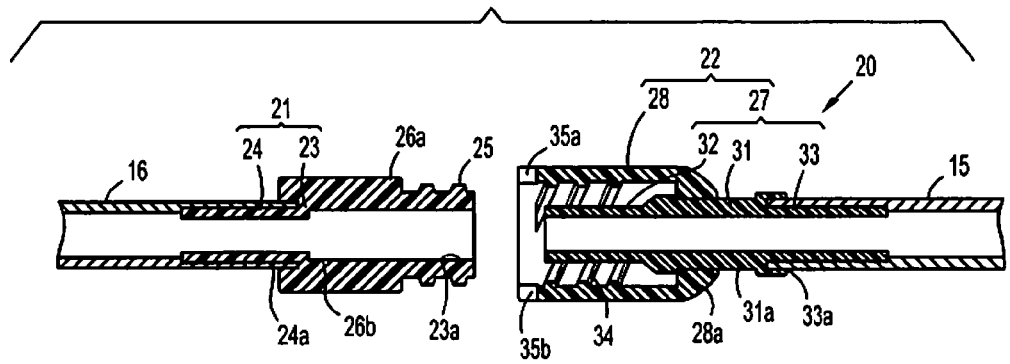
FIG. 8 is a cross-sectional view illustrating the connection structure of the connector before connection between the female connector and the male connector.

When female connector (21) and male connector (22) are connected in connecting structure (20) of the connector with said constitution, first of all, as shown in FIGS. 7 and 8, the tip opening of female connector (21) and the tip opening of male connector (22) are driven to approach each other and face each other. Then, male luer part (32) of male connector (22) is positioned inside female connector (21) and male thread (25) and female thread (34) are brought in contact with each other. Then, lock ring (28) is rotated around the prescribed axis, so that male thread (25) and female thread (34) are screwed to each other.

Figure 9:
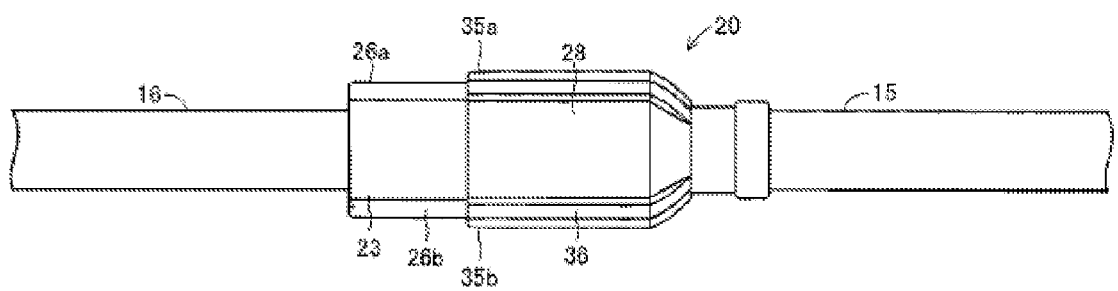
FIG. 9 is a side view illustrating a state of connection between the female connector and the male connector.
Figure 10:
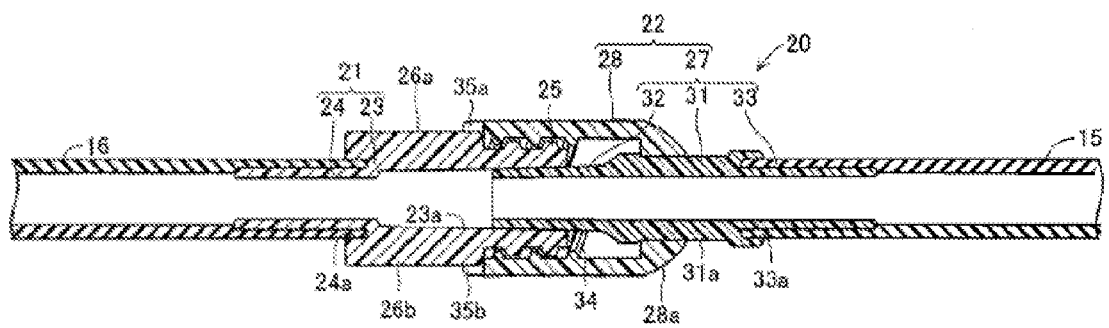
FIG. 10 is a cross-sectional view illustrating a state of connection between the female connector and the male connector.

Then, when lock ring (28) is further rotated, screwing between male thread (25) and female thread (34) reaches an appropriate state, and, as shown in FIGS. 9 and 10, protrusion strips (26a), (26b) of female connector (21) and notches (35a), (35b) of male connector (22) are engaged, respectively. As a result, female connector (21) and male connector (22) are connected in an appropriate connection state free of liquid leakage. In this case, due to engagement between protrusion strips (26a), (26b) and notches (35a), (35b), respectively, female connector (21) cannot rotate with respect to lock ring (28), so that its retreat with respect to male connector (22) can be prevented. As a result, it is possible to maintain an appropriate screwed state between male thread (25) and female thread (34) without loosening of the screwed state between male thread (25) and female thread (34).

When transfusion line set (10) is in use, the downstream end of tube (16) is connected to a holding needle or another piercing member (not shown in the figure) that is to pierce the body of the patient and is to be held there. Then, the liquid medicine is allowed to flow from infusion cylinder (11) into tubes (14), (15), (16). After air in tubes (14), etc. is released to the outside, roller clamp (12) is adjusted to stop the flow of the liquid medicine. In this state, the piercing member is used to pierce into the prescribed portion in the body of the patient, and roller clamp (12) is adjusted to obtain an appropriate flow rate in tubes (14), etc. As a result, the liquid medicine can be fed at a prescribed flow rate into the body of the patient from infusion cylinder (11).

As explained above, for connecting structure (20) in the present embodiment, by rotating lock ring (28) with respect to female connector (21) such that male thread (25) and female thread (34) are screwed to each other, male connector (22) and female connector (21) can be connected to each other. Then, when the screwed state between male thread (25) and female thread (34) becomes appropriate, inner peripheral surface (23a) of female connector (21) and outer peripheral surface of male luer part (32) are in liquid tight contact with each other, and, at the same time, protrusion strips (26a), (26b) of female connector (21) are engaged with corresponding notches (35a), (35b) of lock ring (28), respectively.

Consequently, it is possible to prevent the following problems: development of cracks on female connector (21) or lock ring (28) when male thread (25) and female thread (34) are screwed together too tightly, or leakage of liquid medicine through a gap developed between lock ring (28) and female connector (21) when male thread (25) and female thread (34) are screwed together too loosely. Further, when protrusion strips (26a), (26b) and notches (35a), (35b) are engaged with each other, a clicking sound can be heard, so that a worker can confirm that protrusion strips (26a), (26b) and notches (35a), (35b) are engaged with each other correctly. As a result, correct connection is possible.

In addition, because two groups, that is, protrusion strips (26a), (26b) and notches (35a), (35b), are set, reliable engagement between protrusion strips (26a), (26b) and notches (35a), (35b) can be ensured. As a result, protrusion strips (26a), (26b) and notches (35a), (35b) can hardly separate. Further, since protrusion strips (26a), (26b) are formed as protrusion strips extending in the axial direction of female connector (21), when female connector (21) is manipulated, said protrusion strips (26a), (26b) act to prevent slippage. Further still, protrusion strips (26a), (26b) act as ribs for reinforcement so that the strength of female connector (21) is augmented.

The connection structure of the connector of the present invention is not limited to the aforementioned embodiments. Appropriate changes may be adopted. For example, in said embodiment, infusion cylinder (11) is set in transfusion line set (10). However, one may also adopt a scheme in which the connection structure of the connector is used in connecting tube members for blood transfusion and other purposes in addition to a liquid medicine transfusion line. Additionally, in said embodiment, the engagement protrusion portion is composed of protrusion strips (26a), (26b) extending in the axial direction of female connector (21). However, the engagement protrusion portion may also be formed as short protrusions. Further, the number of engagement protrusions and notch portions is not limited to two groups. One may also adopt one group or more than two groups. In addition, for the constitution of the portions other than the connecting structure of the connector of the present invention, appropriate changes may be made within the technical range of the present invention.

For the connecting structure of a connector pertaining to the present invention with said constitution, by rotating the lock ring with respect to the female connector to screw the male thread and female thread to each other, it is possible to connect the male connector and female connector to each other. In this case, while a male luer portion is formed on the male connector, a female luer portion is formed on the female connector, so that when the male luer portion and female luer portion are connected to each other, the male luer portion is inserted in the female luer portion and the female luer portion and male luer portion are connected while the male thread and female thread are screwed to each other. As a result, while the connection state of the female luer portion and the male luer portion are maintained, the male connector and female connector can be connected to each other. When the screwing state of the male thread and female thread becomes appropriate, the engagement protrusion formed on the outer surface of the female connector and the notch portion formed on the tip portion of the lock ring are engaged with each other.

In this case, the appropriate state of screwing means that the fastening of the male thread and female thread is neither too strong nor too weak, and, in this appropriate fastening state, leakage of liquid does not occur. Consequently, when the deformable part and the notch portion are engaged with each other, by stopping rotation of the lock ring with respect to the female connector, it is possible to avoid the problem of crack formation on the female connector or lock ring due to overly tight fastening of the male thread and female thread or leakage of liquid medicine through a gap generated between the lock ring and the female connector due to overly weak fastening between the male thread and female thread.

Additionally, the connecting structure of the connector of the present invention wherein said male-side connector is composed of a male-side connector main body and said lock ring; the male-side connector main body is composed of a male luer portion formed in a tapered shape with its outer peripheral surface gradually becoming finer from the base end side to the tip side, a supporting portion that supports said lock ring such that it can rotate in the circumferential direction with the outer peripheral surface formed on the rear side of said male luer portion, and a connecting portion formed on the rear side of said supporting portion and connected to said one tube body, and, at the same time, the inner peripheral surface of said female-side connector is formed with a tapered surface that can make liquid tight contact with the outer peripheral surface of said male luer portion; when said male luer portion enters said female-side connector, and the inner peripheral surface of said female-side connector and the outer peripheral surface of said male luer portion are in liquid tight contact with each other, said engagement protrusion and said notch portion are engaged with each other.

As a result, when the tip portion of the male luer portion with its outer peripheral surface formed in a tapered shape is inserted into the female connector formed with a tapered surface with its inner peripheral surface capable of making liquid tight contact with the outer peripheral surface of the male luer portion, so that the inner peripheral surface of the female connector and the outer peripheral surface of the male luer portion are in liquid tight contact with each other, the male luer portion of the male connector and the female connector are connected to each other without leakage of liquid medicine or other liquid. When this state is reached, the engagement protrusion and the notch portion are engaged with each other. As a result, with the state of engagement between the engagement protrusion and the notch portion maintained, it is possible to realize an appropriate state of screwing between the male thread and female thread, and an excellent connection state between the male connector and female connector can be realized.

In addition, the connecting structure of the connector of the present invention is characterized by the fact that when said engagement protrusion and said notch portion are engaged with each other, when the peripheral portion of the notch portion in said lock ring is driven to move so that it climbs over said engagement protrusion, and said engagement protrusion enters the interior of said notch portion, the engagement between said engagement protrusion and said notch portion can be confirmed by means of vibration or sound.

In this case, as the material for forming said lock ring, a flexible and recoverable material is preferred since it can deform while the peripheral portion of the notch portion on the lock ring moves and climbs over the engagement protrusion, and the peripheral portion of the notch portion can recover its original state after the engagement protrusion has entered the interior of the notch portion. When the peripheral portion of the notch portion recovers its original state, vibration may take place, and, when the portion on the female connector side is impacted, a weak clicking sound can be heard. As a result, one can correctly detect engagement between the engagement protrusion and the notch portion. Consequently, correct connection is possible.

Additionally, the connecting structure of the connector of the present invention is characterized by the fact that plural groups of said engagement protrusions and said notch portions are set with a prescribed interval. As a result, engagement between the engagement protrusions and the notch portions can be made more reliable. As a result, separation of the engagement protrusion from the notch portion is even less likely. Consequently, even if a certain external force is applied, an appropriate screwed state can still be maintained between the male thread and female thread, and an excellent connection state between the male connector and the female connector can be maintained.

Further, the connecting structure of the connector of the present invention is characterized by the fact that each said engagement protrusion is made of a protrusion strip extending in the axial direction of said female-side connector. As a result, when the female connector is manipulated, the user's hand can hold the engagement protrusion to prevent slippage, and, at the same time, the engagement protrusion works as a rib to reinforce the female connector.

What is claimed is:

1. A connector, comprising:
 a male-side connector including a male connector main body and a tip portion configured such that an outer peripheral surface of the tip portion and an inner peripheral portion of a base end of the main body form a gap therein, the male-side connecter having a lock ring attached to an outer peripheral side of said male connector main body, wherein a female thread is formed on an inner peripheral surface of the lock ring;
 a female-side connector having a female connector main body and a connecting portion configured such that an outer peripheral surface of the connecting portion and an inner peripheral portion of a base end of the main body form a gap therein, the female-side connector having a male thread formed on an outer peripheral surface of the main body of the female-side connector and wherein at least one engagement protrusion is set to a rear of the male thread;
 at least one notch portion corresponding to the at least one engagement protrusion, the at least one corresponding notch portion set on a tip portion of said lock ring and configured to engage with the engagement protrusion such that when said male thread of said female-side connector and said female thread of said lock ring are screwed together, said at least one engagement protrusion and said at least one corresponding notch portion are engaged with each other; and
 first and second tube bodies, wherein the first tube body is connected to the male-side connector tip portion and positioned such that a tip of the first tube body engages the gap formed between the outer peripheral surface of the tip portion and the inner peripheral portion of the base end of the main body of the male-side connector and wherein the second tube body is connected to the female-side connector such that a tip of the second tube body engages the gap formed between the outer peripheral surface of the connecting portion and the inner peripheral portion of the base end of the main body of the female-side connector such that when said male thread of said female-side connector and said female thread of said lock ring are screwed together, the first tube body and the second tube body are connected to each other via said male-side connector and said female-side connector.

2. The connector according to claim 1, wherein said male connector main body comprises:
- a male luer portion, the male luer portion formed in a tapered shape wherein an outer peripheral surface of the luer portion gradually becomes finer from a base end side to a tip side;
- a supporting portion configured to support said lock ring such that the supporting portion is circumferentially rotatable about an outer peripheral surface formed on a rear side of said male luer portion; and
- a connecting portion formed on a rear side of said supporting portion and connected to said first tube body;
- an inner peripheral surface of said female-side connector is formed with a tapered surface such that a liquid tight contact is formed with the outer peripheral surface of said male luer portion when said male luer portion enters said female-side connector; and
- wherein said male luer portion is configured such that when said male luer portion enters said female-side connector, the inner peripheral surface of said female-side connector and the outer peripheral surface of said male luer portion are in liquid tight contact with each other, and said at least one engagement protrusion and said at least one corresponding notch portion are engaged with each other.

3. The connector according to claim 1, wherein said at least one engagement protrusion and said at least one corresponding notch portion are configured such that said at least one engagement protrusion and said at least one corresponding notch portion are engaged with each other when the peripheral portion of each said at least one corresponding notch portion in said lock ring is driven to move so that it climbs over each said at least one engagement protrusion, and said at least one engagement protrusion enters the interior of each said at least one corresponding notch portion such that the engagement between said at least one engagement protrusion and said at least one corresponding notch portion can be confirmed by means of vibration or sound.

4. The connector according to claim 1, wherein plural groups of engagement protrusions and notch portions are set with a prescribed interval.

5. The connector according to claim 1, wherein each of said at least one engagement protrusion is made of a protrusion strip extending in an axial direction of said female-side connector.

* * * * *